(12) United States Patent
Pierce et al.

(10) Patent No.: US 11,030,923 B2
(45) Date of Patent: Jun. 8, 2021

(54) PIMPLE-POPPING SIMULATOR

(71) Applicants: William Lavern Pierce, Irmo, SC (US); Summer Shantel Pierce, Irmo, SC (US)

(72) Inventors: William Lavern Pierce, Irmo, SC (US); Summer Shantel Pierce, Irmo, SC (US)

(73) Assignee: UNIQUE OBSESSIONS, LLC, Davenport, FL (US)

( * ) Notice: Subject to any disclaimer, the term of this patent is extended or adjusted under 35 U.S.C. 154(b) by 409 days.

(21) Appl. No.: 16/020,489

(22) Filed: Jun. 27, 2018

(65) Prior Publication Data

US 2019/0197922 A1 Jun. 27, 2019

Related U.S. Application Data

(63) Continuation-in-part of application No. PCT/IB2018/051908, filed on Mar. 21, 2018.

(60) Provisional application No. 62/610,343, filed on Dec. 26, 2017.

(51) Int. Cl.
*G09B 23/30* (2006.01)
*A61Q 19/00* (2006.01)
*A61B 17/50* (2006.01)
*A61B 17/00* (2006.01)

(52) U.S. Cl.
CPC ......... *G09B 23/303* (2013.01); *A61Q 19/008* (2013.01); *A61B 17/50* (2013.01); *A61B 2017/00747* (2013.01)

(58) Field of Classification Search
CPC .... G09B 23/28; G09B 23/285; G09B 23/286; G09B 23/30; G09B 23/303
USPC ................................. 434/262, 267, 268, 272
See application file for complete search history.

(56) References Cited

U.S. PATENT DOCUMENTS

| | | | | |
|---|---|---|---|---|
| 4,117,841 A * | 10/1978 | Perrotta | ............... | A61F 13/0206 401/132 |
| 4,493,653 A * | 1/1985 | Robbins | ............... | G09B 23/286 434/218 |
| 4,899,739 A * | 2/1990 | Konishi | ............... | A61F 13/0203 604/306 |
| 5,494,472 A * | 2/1996 | Levy | ........................ | A63H 3/36 428/16 |
| 5,839,904 A * | 11/1998 | Bloom | ................. | G09B 23/285 434/268 |
| 7,306,465 B2 * | 12/2007 | White | ................... | G09B 23/285 434/268 |

(Continued)

*Primary Examiner* — Kurt Fernstrom

(57) ABSTRACT

The pimple-popping simulator is an apparatus that allows a user to practice popping pimples without directly popping a real pimple. The apparatus includes a pliable body, at least one channel, and a quantity of discharge-like filling. The pliable body mirrors supple skin. The at least one channel mirrors a pore. The quantity of discharge-like filling represents the dead skin cells, oils, and bacteria clogged within the pore. The at least one channel further includes a first edge, a second edge, a lateral wall, and a reservoir. The first edge defines a main opening. The second edge prevents the quantity of discharge-like filling from escaping unless the proper force is applied. The lateral wall defines an exit for the quantity of discharge-like filling. The lateral wall preferably tapers from the second edge to the first edge, thereby mirroring the popping of pus of a pimple as a result of pressure.

15 Claims, 6 Drawing Sheets

(56) References Cited

U.S. PATENT DOCUMENTS

| | | | | |
|---|---|---|---|---|
| 7,841,586 B1* | 11/2010 | Mongeon | ............... | B65D 81/22 |
| | | | | 261/104 |
| 8,408,920 B2* | 4/2013 | Speller | ................. | G09B 23/285 |
| | | | | 434/268 |
| 8,535,062 B2* | 9/2013 | Nguyen | ................. | G09B 23/30 |
| | | | | 434/267 |
| 8,944,825 B2* | 2/2015 | Reid-Searl | ............. | G09B 23/30 |
| | | | | 434/267 |
| 2003/0187518 A1* | 10/2003 | Carls | ...................... | A45D 44/00 |
| | | | | 623/59 |
| 2005/0163973 A1* | 7/2005 | Drinkward | ............... | A41G 7/02 |
| | | | | 428/166 |
| 2005/0214727 A1* | 9/2005 | Stoianovici | ............ | G09B 23/28 |
| | | | | 434/262 |
| 2012/0015337 A1* | 1/2012 | Hendrickson | .......... | G09B 23/28 |
| | | | | 434/267 |
| 2014/0329217 A1* | 11/2014 | Barsness | .............. | G09B 23/285 |
| | | | | 434/272 |
| 2020/0035128 A1* | 1/2020 | Ousley | ................ | B29C 66/7486 |

* cited by examiner

//PIMPLE-POPPING SIMULATOR

The current application is a continuation-in-part (CIP) application of a Patent Cooperation Treaty (PCT) application PCT/IB2018/051908 filed on Mar. 21, 2018. The Patent Cooperation Treaty (PCT) PCT/IB2018/051908 claims a priority to a U.S. provisional application Ser. No. 62/610,343 filed on Dec. 26, 2017.

FIELD OF THE INVENTION

The present invention relates generally to pimples. More specifically, the present invention is a pimple-popping simulator that guides a user to properly pop a pimple.

BACKGROUND OF THE INVENTION

Skincare is becoming an increasingly popular obsession for beauty and enthusiasts. One of the most common issues of skincare is clogged pores. Clogged pores may include, but are not limited to, blackheads, whiteheads, and pimples. Clogged pores result from oily skin, dirt and dead cells on the skin, and ingrown hairs. In order to get rid of and prevent clogged pores, various masks and treatments must be applied regularly. However, in the event a pimple has developed as a result of dead skin cells, oil, and bacteria, the most common and quick method of relieving the clogged pore it to pop the pimple. Popping the pimple is not recommended because popping pimples has a higher chance of scarring. If a pimple is popped properly, however, the clogged pore is relieved faster and heals quicker.

As the popularity of relieving clogged pores has risen, so has the realization of the satisfaction that comes with the removal the dirt and oil of clogged pores. Social media and advertisements present the effective and clean removal of blackheads, the popping of pimples, and so on. In addition to the satisfaction of relieving clogged pores in a single attempt, there is also the entertainment factor, or the dirt being removed.

It is an objective of the present invention to simulate the popping of pimples without having to pop real pimples. The present invention allows a user to pop at least one pimple or multiple pimples continuously. The present invention facilitates the proper manner of popping pimples. The present invention may also serve as a stress reliever and a fun toy.

DETAILED DESCRIPTION OF THE INVENTION

All illustrations of the drawings are for the purpose of describing selected versions of the present invention and are not intended to limit the scope of the present invention.

Figure 1:
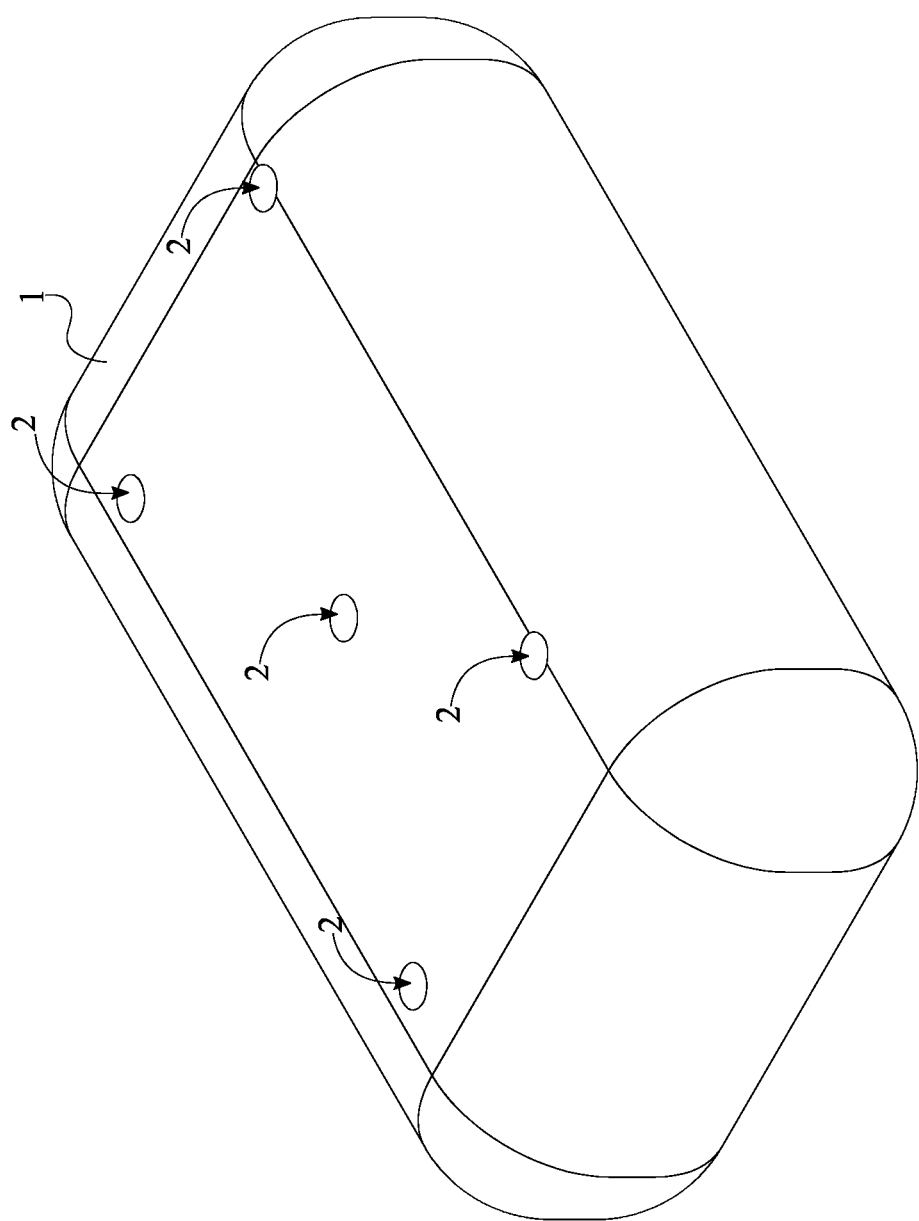
FIG. 1 is a top perspective view of the present invention with the sealing layer separated from the pliable body.
Figure 2:
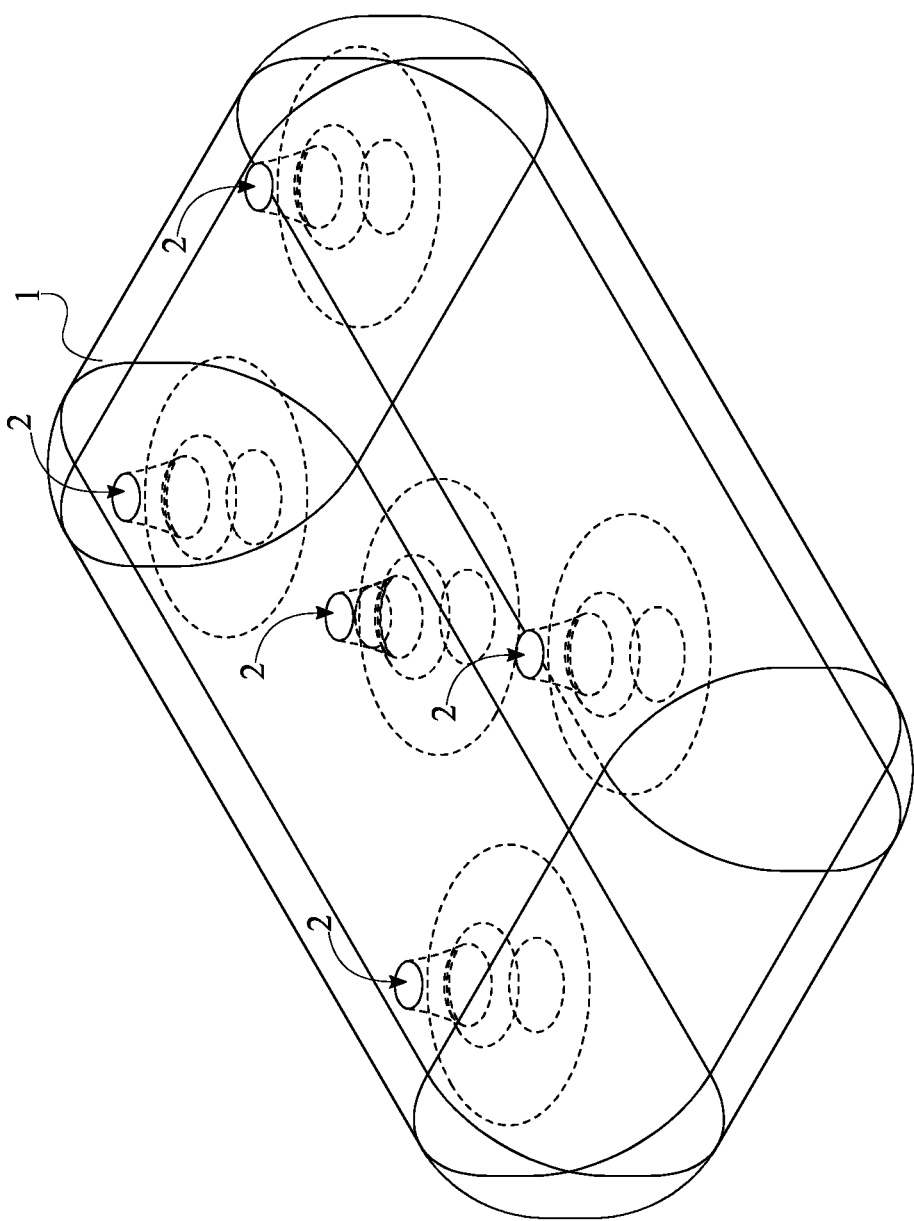
FIG. 2 is a schematic view of the at least one channel traversing into the pliable body of the present invention.

The present invention is a pimple-popping simulator that allows a user to practice popping pimples without having to pop a real pimple. More specifically, the present invention allows the user to continuously practice popping pimples without popping multiple real pimples. The present invention comprises a pliable body 1, at least one channel 2, and a quantity of discharge-like filling 11. As seen in FIG. 1 and FIG. 2, the pliable body 1 allows the quantity of discharge-like filling 11 housed within the at least one channel 2 to be pressed out of the at least one channel 2. The pliable body 1 mirrors the suppleness of skin. In the preferred embodiment of the present invention, the pliable body 1 is made of non-toxic silicone material. The at least one channel 2 houses the quantity of discharge-like filling 11, like that of a pore containing dead skin cells, bacteria, and oil. The at least one channel 2 allows the quantity of discharge-like filling 11 to be contained within the skin like that of a clogged pore. In order to contain the quantity of discharge-like filling 11, the at least one channel 2 comprises a first edge 3, a second edge 5, a lateral wall 6, and a reservoir 7. The first edge 3 prevents the quantity of discharge-like filling 11 from escaping the at least one channel 2 and requires that a force is applied around the first edge 3 in order to push the quantity of discharge-like filling 11 from out of the at least one channel 2. The second edge 5 prevents the quantity of discharge-like filling 11 from leaking past the reservoir 7 and traversing across the lateral wall 6. The lateral wall 6 further secures the quantity of discharge-like filling 11 within the reservoir 7 and allows the quantity of discharge-like filling 11 to exit the at least one channel 2 in the same manner as that of a real pimple or clogged pore. The reservoir 7 houses the quantity of discharge-like filling 11. The quantity of discharge-like filling 11 represents a clogged pore, more specifically the quantity of discharge-like filling 11 represents the pus within a pimple. In alternate embodiments of the present invention, the quantity of discharge-like filling 11 may also mirror a blackhead, a whitehead, and so on. In the preferred embodiment of the present invention, the quantity of discharge-like filling 11 comprises a quantity of beeswax and a quantity of oil. The quantity of beeswax and the quantity of oil is homogeneously mixed with each other in order to physically and visually mirror discharge of a clogged pore. In alternate embodiments of the present invention, quantity of discharge-like filling 11 may comprise varying quantities and combinations of beeswax and oil in order to represent a variety of discharges. The quantity of oil may be, but is not limited to olive oil, canola oil, and extra virgin olive oil. Alternate embodiments of the present invention may comprise additional ingredients such as flaxseed gel and coconut oil in order to alter the consistency and appearance of the quantity of discharge-like filling 11.

Figure 3:
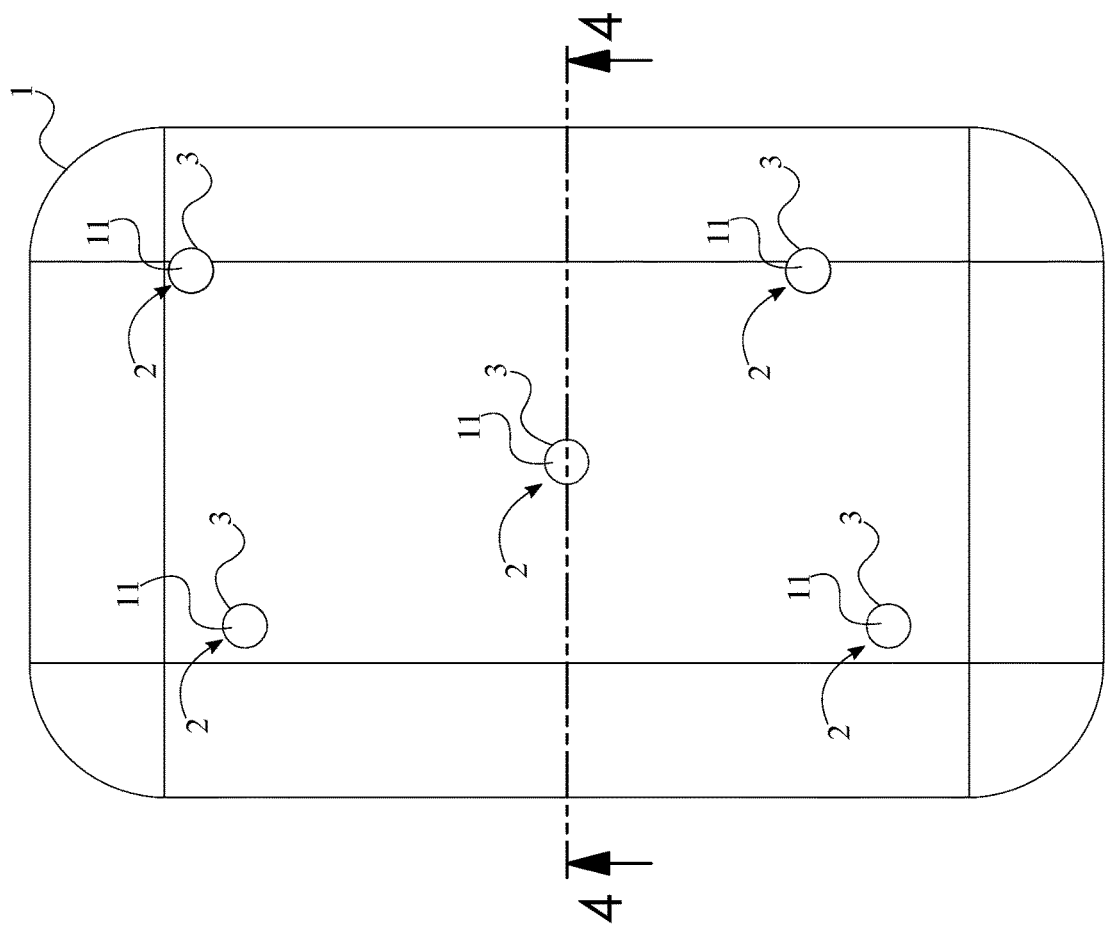
FIG. 3 is a top side view of the present invention with the sealing layer separated from the pliable body.

The overall arrangement allows the quantity of discharge-like filling 11 to be housed within the pliable body 1 and released the quantity of discharge-like filling 11 with the appropriate amount of force. In order to contain the quantity of discharge-like filling 11 within the pliable body 1, the at least one channel 2 traverses into the pliable body 1 from a top surface 15 of the pliable body 1, seen in FIG. 2, FIG. 4, and FIG. 5. In the preferred embodiment of the present invention the at least one channel 2 comprises a plurality of channels, seen in FIG. 1 and FIG. 3, allowing the user to continuously simulate the popping of pimples. The plurality of channels is arbitrarily distributed across the pliable body 1 in order to represent multiple pimples of a surface of skin. In order to release the quantity of discharge-like filling 11 from within the reservoir 7, the first edge 3 is positioned opposite the second edge 5 about the lateral wall 6, and a main opening 4 is delineated by the first edge 3. Moreover, the main opening 4 is positioned adjacent to the top surface 15 in order for the main opening 4 to serve as an exit for the quantity of discharge-like filling 11. The arrangement of the lateral wall 6 with that of the main opening 4 shapes the quantity of discharge-like filling 11 upon the exit of the at least one channel 2. The present invention facilitates the removal of the quantity of discharge-like filling 11 only if the appropriate force is applied around the first edge 3, as the reservoir 7 is perimetrically connected to the second edge 5 and is integrated into the pliable body 1. Moreover, the quantity of discharge-like filling 11 is positioned within the reservoir 7. The quantity of discharge-like filling 11 escapes the pliable body 1 with applied pressure against the top surface 15 as the reservoir 7 is in fluid communication with the main opening 4 through lateral wall 6.

Figure 4:
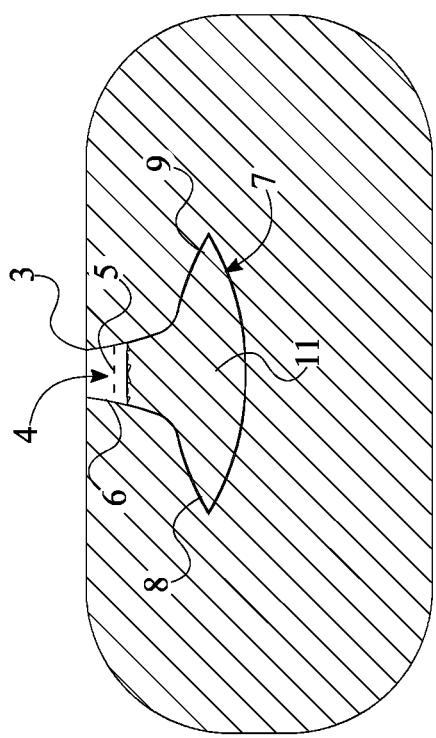
FIG. 4 is a cross-sectional view of FIG. 3 along line 4-4.
Figure 5:
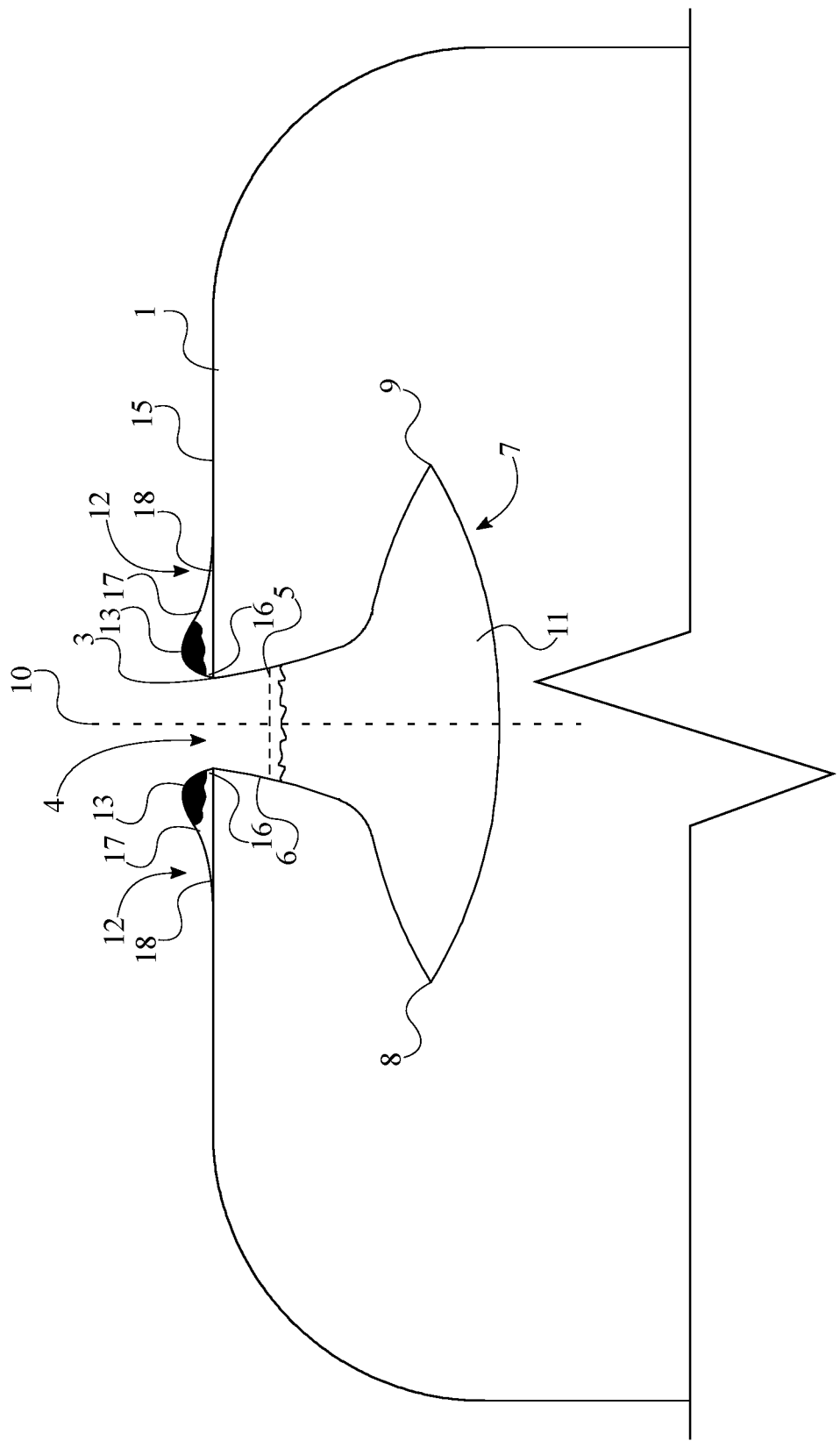
FIG. 5 is a schematic view of the at least one channel of the present invention with the elevated rim and the visual indicator.
Figure 6:
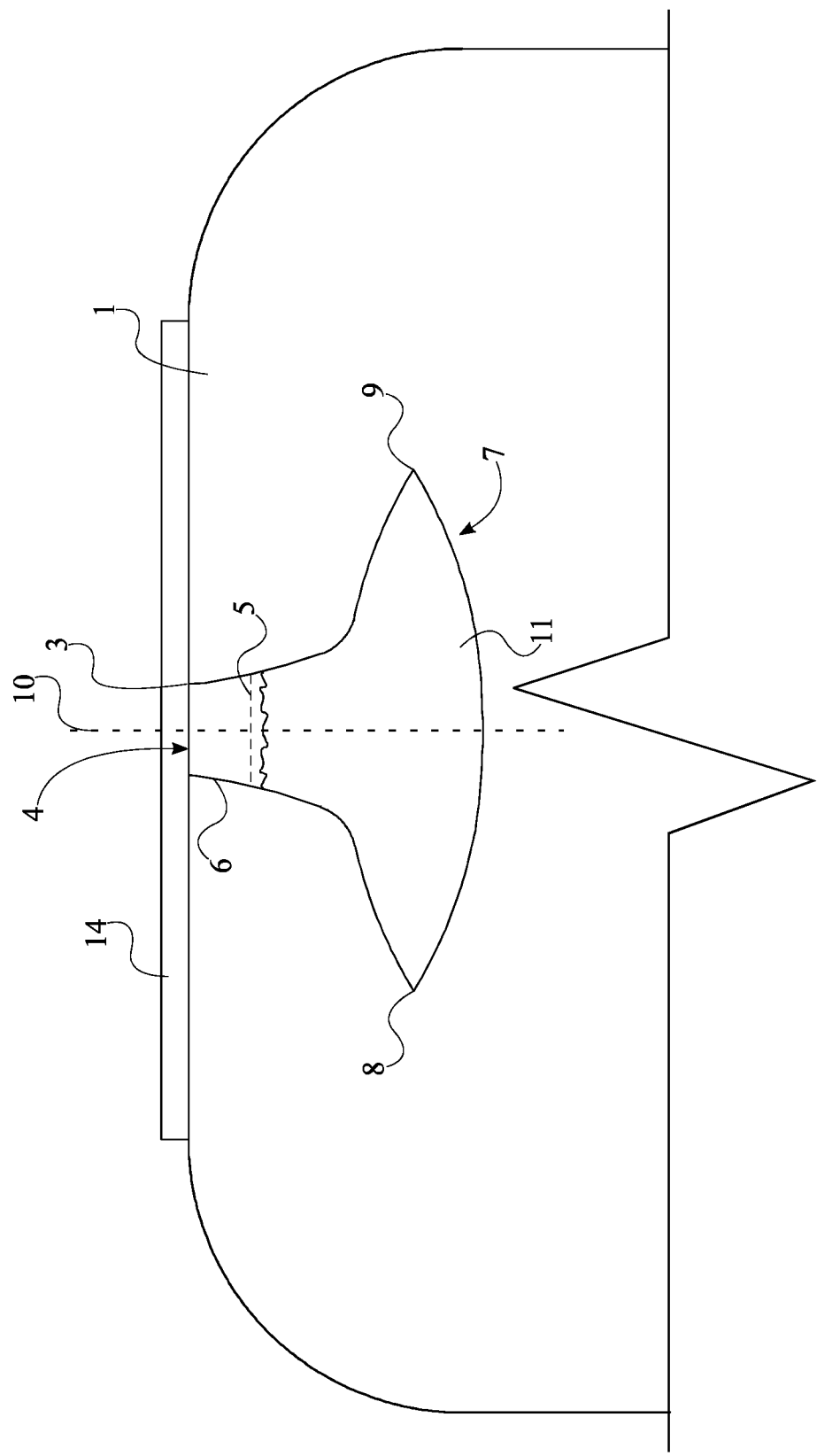
FIG. 6 is a schematic view of the opening of the at least one channel covered with the sealing layer of the present invention.

As shown in FIG. 4, FIG. 5, and FIG. 6, in the preferred embodiment of the present invention, the lateral wall 6 tapers from the second edge 5 to the first edge 3. This allows the applied force against the pliable body 1 and around the first edge 3 to create pressure within the reservoir 7. Moreover, the pressure then builds between the second edge 5 and the first edge 3 allows the quantity of discharge-like filling 11 to pop out of the main opening 4 similar to that of a real pimple. Furthermore, in the preferred embodiment of the present invention, the reservoir 7 comprises a first end 8 and a second end 9. The first end 8 and the second end 9 both serve as position-placement indicators for the applied force of a user against the pliable body 1 and around the first edge 3. In order to effectively practice popping pimples, the reservoir 7 tapers from a sagittal plane 10 of the at least one channel 2 to the first end 8. Similarly, the reservoir 7 tapers from the sagittal plane 10 of the at least one channel 2 to the second end 9. More specifically, the reservoir 7 preferably comprises a football-shape.

An alternate embodiment of the present invention comprises an elevated rim 12, shown in FIG. 5. The elevated rim 12 properly angles the force of the user and positions the fingers of the user against the pliable body 1 and around the first edge 3. The elevated rim 12 mirrors the inflammation of the skin around a clogged pore. In order for the force against the elevated rim 12 to create pressure within the reservoir 7, the elevated rim 12 is integrated onto the pliable body 1, is integrated onto the top surface 15, and is perimetrically positioned around the first edge 3 of the at least one channel 2. The elevated rim 1 comprises an inside section 16, an intermediate section 17, and an outside section 18. The inside section 16 is positioned adjacent to the first edge 3. The outside section 18 is positioned away from the first edge 3. The intermediate section 17 is positioned in between the inside section 16 and the outside section 18. A thickness of the intermediate section 17 is larger than each of a thickness of the inside section 16 and a thickness of the outside section 18. In order for the user to better identify the elevated rim 12, an alternate embodiment may further comprise a visual indicator 13. The visual indicator 13 is preferably a pigmentation, a redness within the elevated rim 12. Moreover, the visual indicator 13 is integrated into the elevated rim 12, wherein the visual indicator 13 represents inflammation of the skin.

In order to preserve the quantity of discharge-like filling 11 within the reservoir 7, the preferred embodiment of the present invention comprises a sealing layer 14, shown in FIG. 6. The sealing layer 14 is preferably flexible and made of plastic. The sealing layer 14 is adhered across the pliable body 1 in order to preserve the consistency of the quantity of discharge-like filling 11. Furthermore, the sealing layer 14 is positioned adjacent the main opening 4. This arrangement prevents the unwanted escape of the quantity of discharge-like filling 11 from within the reservoir 7, past the first edge 3 of the at least one channel 2.

In order to effectively use the present invention, the user removes the sealing layer 14 from the pliable body 1, shown in FIG. 5. The user identifies the first edge 3 of the at least one channel 2, seen in FIG. 3, FIG. 4, and FIG. 5, and positions at least two fingers about the first edge 3. The user applies force with the at least two fingers against the pliable body 1 until the quantity of discharge-like filling 11 escapes from the main opening 4. The quantity of discharge-like filling 11 pops out of the at least one channel 2 similar to that of a pimple or clogged pore.

Although the invention has been explained in relation to its preferred embodiment, it is to be understood that many other possible modifications and variations can be made without departing from the spirit and scope of the invention as hereinafter claimed.

What is claimed is:

1. A pimple-popping simulator comprises:
   a pliable body;
   at least one channel;
   a quantity of discharge-like filling;
   the at least one channel comprises a first edge, a second edge, a lateral wall, and a reservoir;
   the at least one channel traversing into the pliable body from a top surface of the pliable body;
   the first edge being positioned opposite the second edge about the lateral wall;
   a main opening being delineated by the first edge;
   the main opening being positioned adjacent to the top surface;
   the reservoir being perimetrically connected to the second edge;
   the reservoir being integrated into the pliable body;
   the quantity of discharge-like filling being positioned within the reservoir;
   the reservoir being in fluid communication with the main opening through lateral wall;
   an elevated rim;
   the elevated rim being integrated onto the top surface;
   the elevated rim being perimetrically positioned around the first edge;
   the elevated rim comprising an inside section, an intermediate section and an outside section;
   the inside section being positioned adjacent to the first edge;
   the outside section being positioned away from the first edge;
   the intermediate section being positioned in between the inside section and the outside section; and
   a thickness of the intermediate section being larger than each of a thickness of the inside section and a thickness of the outside section.

2. The pimple-popping simulator as claimed in claim 1 comprises:
   the at least one channel comprises a plurality of channels; and
   the plurality of channels being distributed across the pliable body.

3. The pimple-popping simulator as claimed in claim 1, wherein the lateral wall being tapered from the second edge to the first edge.

4. The pimple-popping simulator as claimed in claim 1 comprises:
the reservoir comprises a first end and a second end;
the reservoir being tapered from a sagittal plane of the at least one channel to the first end; and
the reservoir being tapered from the sagittal plane of the at least one channel to the second end.

5. The pimple-popping simulator as claimed in claim 1 comprises:
a visual indicator; and
the visual indicator being integrated into the elevated rim, wherein the visual indicator represents inflammation of skin.

6. The pimple-popping simulator as claimed in claim 1, wherein the pliable body is made of non-toxic silicone material.

7. The pimple-popping simulator as claimed in claim 1, wherein the quantity of discharge-like filling comprises a quantity of beeswax and a quantity of oil; and the quantity of beeswax and the quantity of oil being homogenously mixed with each other.

8. The pimple-popping simulator as claimed in claim 1 comprises:
a sealing layer;
the sealing layer being adhered across the pliable body; and
the sealing layer being positioned adjacent the main opening.

9. A pimple-popping simulator comprises:
a pliable body;
at least one channel;
a quantity of discharge-like filling;
a sealing layer;
the at least one channel comprises a first edge, a second edge, a lateral wall, and a reservoir;
the at least one channel traversing into the pliable body from a top surface of the pliable body;
the first edge being positioned opposite the second edge about the lateral wall;
a main opening being delineated by the first edge;
the main opening being positioned adjacent to the top surface;
the reservoir being perimetrically connected to the second edge;
the reservoir being integrated into the pliable body;
the quantity of discharge-like filling being positioned within the reservoir,
the reservoir being in fluid communication with the main opening through lateral wall;
the sealing layer being adhered across the pliable body;
the sealing layer being positioned adjacent the main opening;
an elevated rim;
the elevated rim being integrated onto the top surface;
the elevated rim being perimetrically positioned around the first edge;
the elevated rim comprising an inside section, an intermediate section and an outside section;
the inside section being positioned adjacent to the first edge;
the outside section being positioned away from the first edge;
the intermediate section being positioned in between the inside section and the outside section; and
a thickness of the intermediate section being larger than each of a thickness of the inside section and a thickness of the outside section.

10. The pimple-popping simulator as claimed in claim 9 comprises:
the at least one channel comprises a plurality of channels; and
the plurality of channels being distributed across the pliable body.

11. The pimple-popping simulator as claimed in claim 9, wherein the lateral wall being tapered from the second edge to the first edge.

12. The pimple-popping simulator as claimed in claim 9 comprises:
the reservoir comprises a first end and a second end;
the reservoir being tapered from a sagittal plane of the at least one channel to the first end; and
the reservoir being tapered from the sagittal plane of the at least one channel to the second end.

13. The pimple-popping simulator as claimed in claim 9 comprises:
a visual indicator; and
the visual indicator being integrated into the elevated rim, wherein the visual indicator represents inflammation of skin.

14. The pimple-popping simulator as claimed in claim 9, wherein the pliable body is made of non-toxic silicone material.

15. The pimple-popping simulator as claimed in claim 9, wherein the quantity of discharge-like filling comprises a quantity of beeswax and a quantity of oil; and the quantity of beeswax and the quantity of oil being homogenously mixed with each other.

\* \* \* \* \*